(12) United States Patent
Dalton et al.

(10) Patent No.: US 8,920,390 B2
(45) Date of Patent: Dec. 30, 2014

(54) VASCULAR ACCESS PORT WITH TUBULAR SHAPED SEPTUM

(76) Inventors: Michael J. Dalton, Evanston, IL (US);
Jordan M. Dalton, Chicago, IL (US);
Natan A. Pheil, Chicago, IL (US)

( * ) Notice: Subject to any disclaimer, the term of this patent is extended or adjusted under 35 U.S.C. 154(b) by 222 days.

(21) Appl. No.: 13/410,302

(22) Filed: Mar. 2, 2012

(65) Prior Publication Data

US 2013/0060200 A1 Mar. 7, 2013

Related U.S. Application Data

(60) Provisional application No. 61/454,527, filed on Mar. 19, 2011.

(51) Int. Cl.
*A61M 31/00* (2006.01)
*A61M 39/02* (2006.01)

(52) U.S. Cl.
CPC ..... *A61M 39/0208* (2013.01); *A61M 2039/022* (2013.01); *A61M 2039/0226* (2013.01); *A61M 2039/0229* (2013.01)
USPC ............. 604/288.02; 604/288.01; 604/288.04

(58) Field of Classification Search
USPC .......................... 604/288.01, 288.02, 288.04
See application file for complete search history.

(56) References Cited

U.S. PATENT DOCUMENTS

| 4,767,410 | A  | * | 8/1988  | Moden et al. ................. 604/175 |
| 5,137,529 | A  | * | 8/1992  | Watson et al. ............. 604/891.1 |
| 7,846,139 | B2 | * | 12/2010 | Zinn et al. ................. 604/288.03 |
| 2005/0131325 | A1 | * | 6/2005  | Chen et al. ....................... 602/41 |
| 2008/0119798 | A1 | * | 5/2008  | Chantriaux et al. ...... 604/288.02 |

* cited by examiner

*Primary Examiner* — Laura Bouchelle
(74) *Attorney, Agent, or Firm* — Skokos Law Group LLC; Soula Skokos

(57) ABSTRACT

A vascular access port having a novel septum design that while allowing for larger septum access area and larger degree of access allows for an overall small profile. The present invention further provides for a novel septum and reservoir design that eliminates angular junctions.

31 Claims, 31 Drawing Sheets

SCALE 6:1

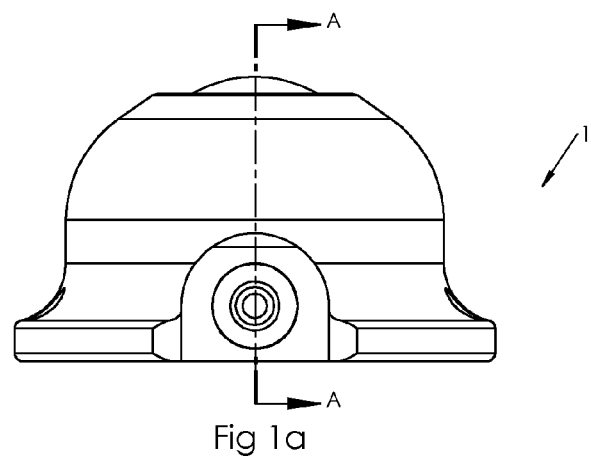
Fig 1a
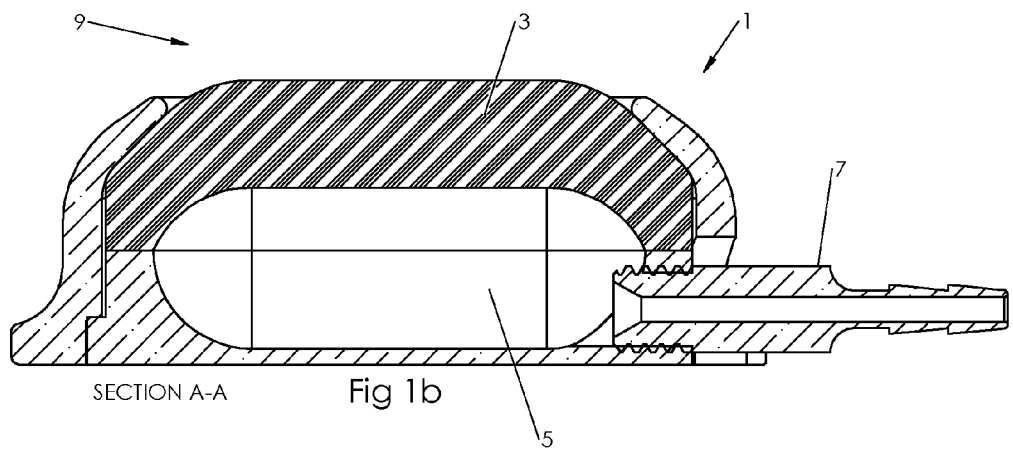
SECTION A-A    Fig 1b
SCALE 6:1

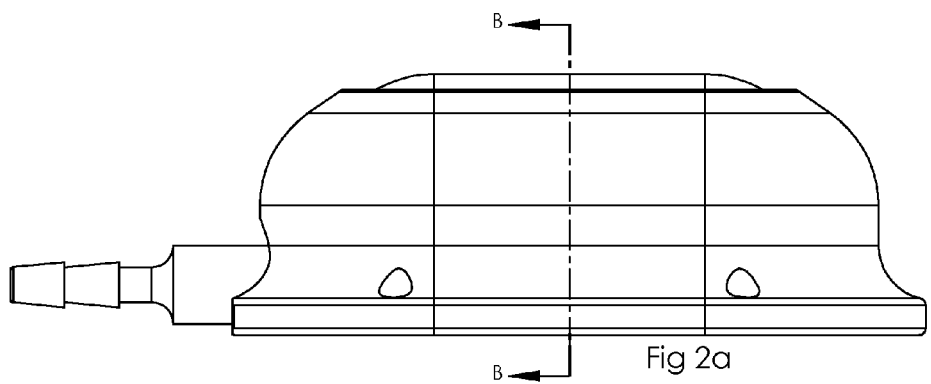
Fig 2a
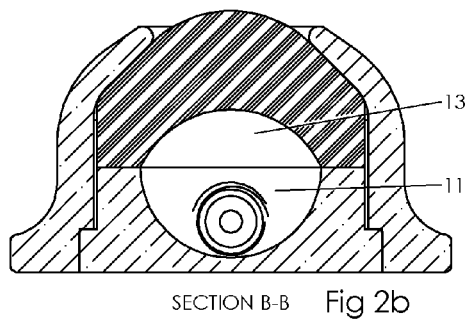
SECTION B-B   Fig 2b
SCALE 6:1

SCALE 6:1

SCALE 6:1

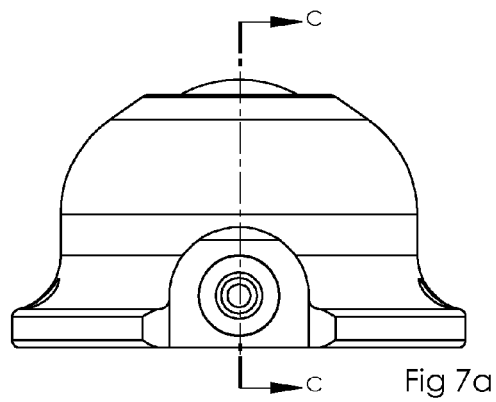
Fig 7a
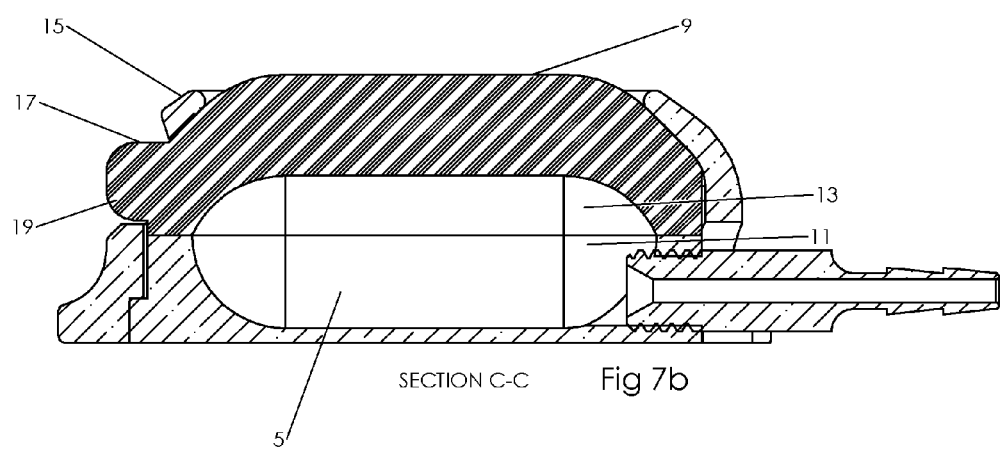
SECTION C-C  Fig 7b
SCALE 6:1

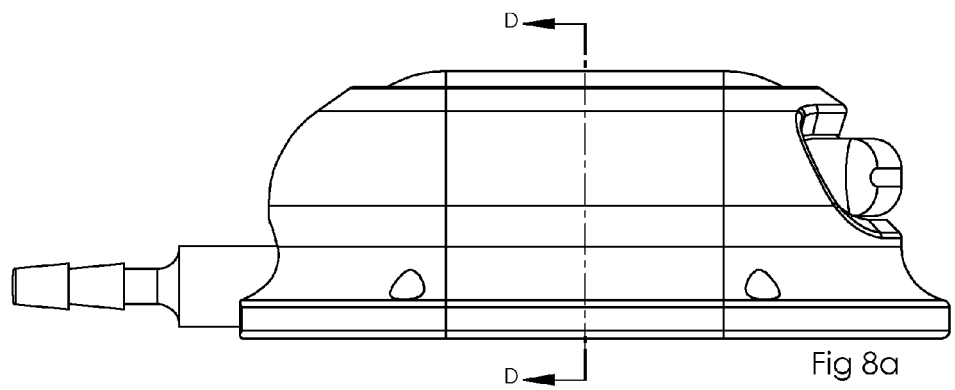
Fig 8a
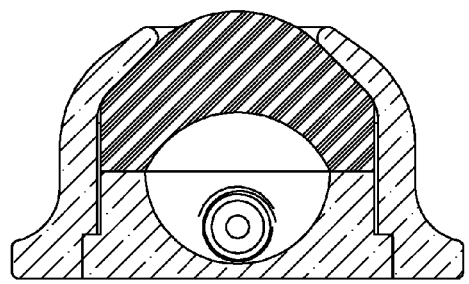
SECTION D-D    Fig 8b
SCALE 6:1

SCALE 6:1

SCALE 6:1

SCALE 6:1

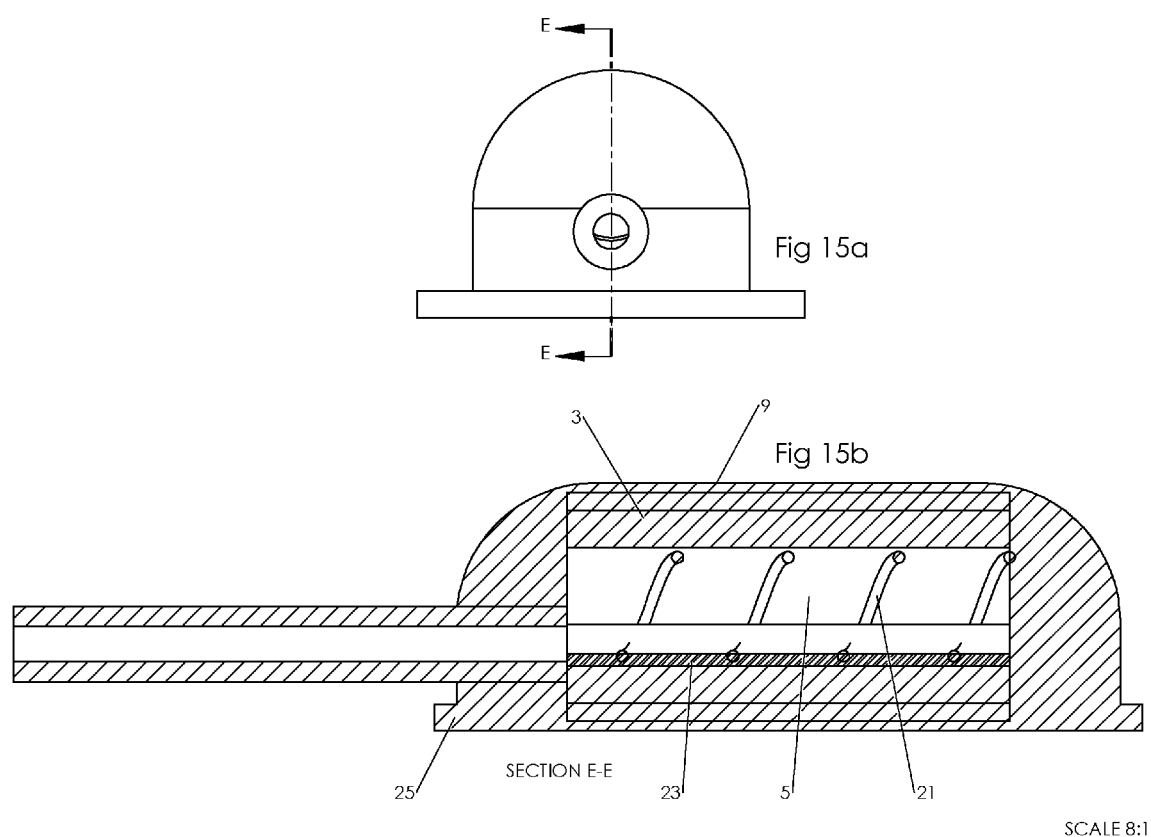

SCALE 8:1

SCALE 8:1

SCALE 8:1

SCALE 8:1

SCALE 8:1

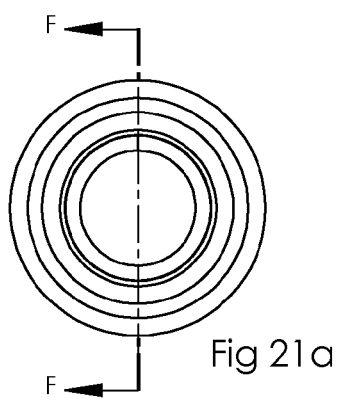
Fig 21a
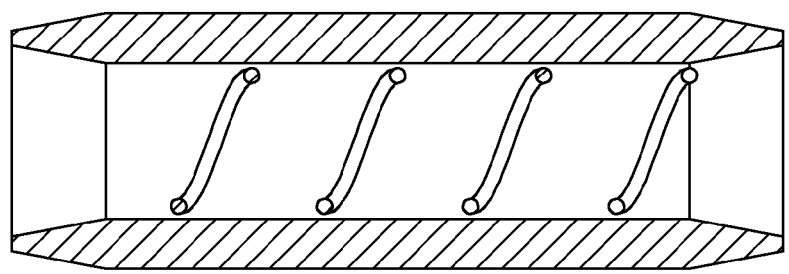
SECTION F-F    Fig 21b
SCALE 8:1

SCALE 8:1

SCALE 8:1

SECTION G-G

SCALE 6:1

SCALE 6:1

SCALE 6:1

SCALE 4:1

SCALE 4:1

SCALE 4:1

VASCULAR ACCESS PORT WITH TUBULAR SHAPED SEPTUM

CROSS REFERENCE

This application claims priority from U.S. Provisional Patent Application Ser. No. 61/454,527, filed Mar. 19, 2011 of the same title.

FIELD OF THE INVENTION

The present invention relates to implantable medical devices for subcutaneous implantation and which can be accessed through the skin, such as with a needle coupled to a syringe for delivery of therapeutic preparations into the vascular structure of the patient. More particularly, this invention relates to access ports which may be accessed parallel to the skin or have a 180 degree access area.

BACKGROUND OF THE INVENTION

Subcutaneously implanted vascular access devices, or ports, have been used for many years to provide long term vascular access in patients that require frequent or periodic therapeutic infusions or blood draws. Currently, ports generally have a reservoir body that contains a chamber accessible by a self-sealing septum and an outlet that is connected to a catheter that is placed into the vascular system. The port is implanted into a subcutaneous pocket during a minor surgical procedure.

A disadvantage of current devices is that they generally possess a cylindrical reservoir having a circular access area to be accessed by the user. The use of a cylindrical reservoir, however, creates "corners" or angular junctions, specifically where the bottom wall of the reservoir meets the continuous side wall. The design of a cylindrical reservoir will necessarily require the side wall of the reservoir to meet the bottom wall at or about a ninety degree angle. One example of a cylindrical reservoir in an implantable infusion port is disclosed in U.S. Pat. No. 4,673,394. Although cylindrically shaped reservoirs are commonly used in such implantable devices, the angular junctions in such reservoirs may pose significant health risks to the patient over time. A major issue with implantable infusion ports is the accumulation of debris and residue over time that may eventually lead to the occlusion of the device. With current port technology, such angular junctions are present not only where the bottom wall of the reservoir meets the continuous side wall, but also where the continuous side wall meets the planar septum covering the reservoir. The use of a generally planar septum to cover the cylindrical reservoir creates an additional angular junction where the side wall of reservoir meets the planar septum. The current technology, therefore, teaches a 90 degree angled junction at both the perimeter of the bottom wall and the top edge of the side wall where the side wall meets the bottom surface of the septum thereby creating a large area in which debris and residue can accumulate and cause complications for the user. A significant drawback of the current technology is that the design of the reservoir and septum provides ample opportunity for debris and residue to accumulate which may compromise the safety of the patient over time.

What is required, therefore, is an implantable vascular access port that overcomes the drawbacks of the current technology by having a novel reservoir and septum design that attempts to eliminate angular junctions and include flow patterns within the reservoir.

In recent years, there has been a development of smaller profile ports for implantation in smaller subcutaneous spaces, such as in a patient's arm. The smaller the port; however, the smaller the septum access area must be to accomplish a small profile. A need, therefore, exists for a vascular port that provides for a smaller profile but that allows for substantial septum access area.

There has been a further development of ports having an elongated body and non-circular septum access area, such as in U.S. Pat. No. 7,850,666. While such an elongated body may provide a non-circular septum access area, it does not address the disadvantages of a cylindrically shaped reservoir since the septum is planar. The use of a planar septum and cylindrical reservoir will necessarily result in corners at the junction of the bottom and side walls of the reservoir and where the side wall meets the bottom surface of the septum. Such a design provides ample opportunity for debris and residue to accumulate over time.

Accordingly, a need exists for a vascular access port which provides a small profile for insertion through a small incision and a larger septum access area or degree of access having a novel septum and reservoir design that attempts to eliminate angular junctions and include flow patterns within the reservoir.

SUMMARY OF THE INVENTION

The present invention provides a vascular access port having a novel septum design that while allowing for larger septum access area and larger degree of access, the port is able to have an overall small profile. The present invention further provides for a novel septum and reservoir design that eliminates angular junctions.

In one embodiment, the self-sealing septum is comprised of a shell-like structure enclosing a fluid reservoir therein. The self-sealing septum may have an access portion or area that is exposed to the subcutaneous tissue and may be accessed through the use of an infusion needle. Unlike current vascular access ports, the self-sealing septum does not simply cover the reservoir body and provide means by which to access the reservoir, but rather the structure of the septum itself forms a portion of the fluid reservoir. In the present invention, the septum resembles a shell having a wall of a predetermined thickness thereby creating a reservoir or chamber. The benefit of the present invention over the prior art is that the shell-like structure of the septum allows for a much greater area of the septum exposed to the subcutaneous tissue and thereby creates a much larger area that can be accessed by the user.

The shape of the self-sealing septum in the plane of the septum may be of any conventional shape such as circular, elliptical, tubular, cylindrical, rectilinear, polygonal or triangular. The area of the septum that is exposed to the subcutaneous tissue or skin surface is independent of the size and shape of the septum The present invention further has an outlet stem leading from the septum's reservoir, or chamber, to a catheter that is placed into the vascular system. Most preferably, a lip is formed around the bottom perimeter of the septum through which sutures can pass to secure the device to the deep fascia to ensure that the device remains in the proper location and not migrate or flip over time.

BRIEF DESCRIPTION OF THE DRAWINGS

FIG. 1a is front view of a skin parallel vascular access port designed in accordance with an embodiment of the present invention;

FIG. 1b is a cross sectional view of a skin parallel vascular access port designed in accordance with an embodiment of the present invention;

FIG. 2a is a side view of a skin parallel vascular access port designed in accordance with an embodiment of the present invention;

FIG. 2b is a side cross sectional view of a skin parallel vascular access port designed in accordance with an embodiment of the present invention;

FIG. 7a is a front view of an embodiment of the skin parallel vascular access port;

FIG. 7b is a side cross sectional view of an embodiment of the skin parallel vascular access port;

FIG. 8a is a side view of an embodiment of the skin parallel vascular access port;

FIG. 8b is a front cross sectional view of an embodiment of the skin parallel vascular access port;

FIG. 15a is a front view of an embodiment of the skin parallel vascular access port wherein the septum's reservoir or chamber leads to an attached catheter;

FIG. 15b is a side cross sectional view of an embodiment of the skin parallel vascular access port wherein the septum's reservoir or chamber leads to an attached catheter;

FIG. 21 is a cross sectional view of an embodiment of the present invention wherein the present invention is a shunt;

DETAILED DESCRIPTION OF THE DRAWINGS

Figure 3:
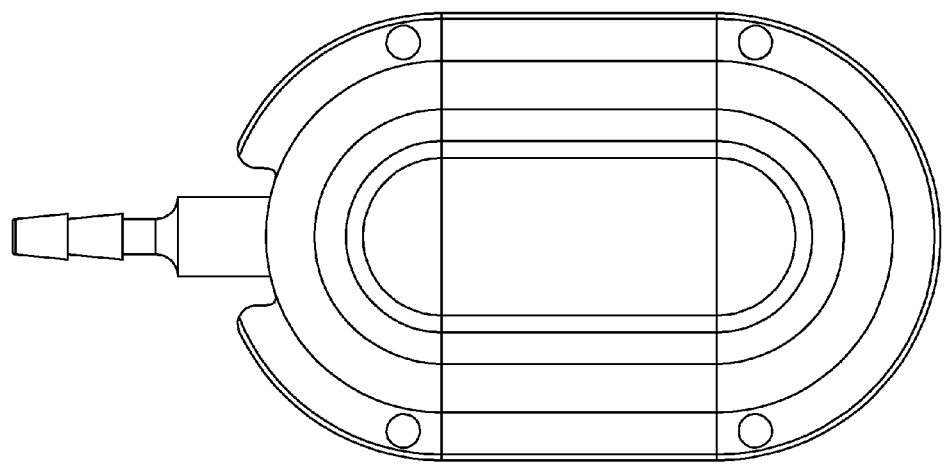
FIG. 3 is a top view of a skin parallel vascular access port designed in accordance with an embodiment of the present invention.
Figure 4:
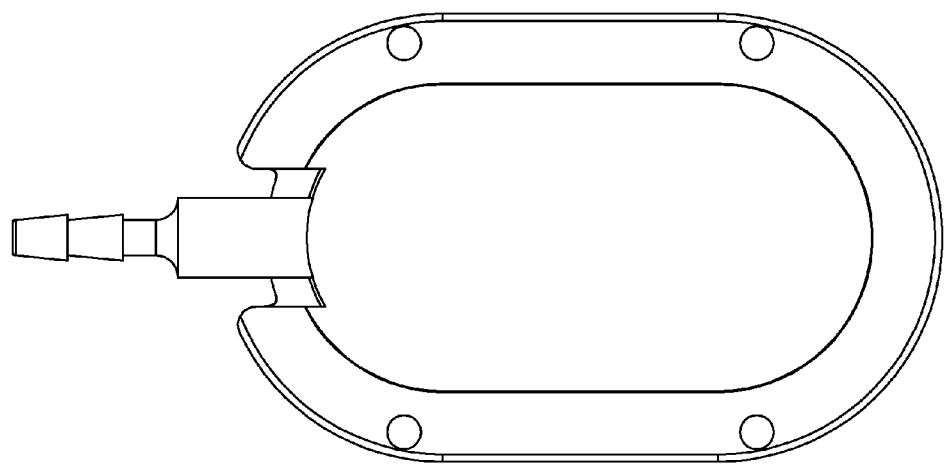
FIG. 4 is a bottom view of a skin parallel vascular access port designed in accordance with an embodiment of the present invention.
Figure 5:
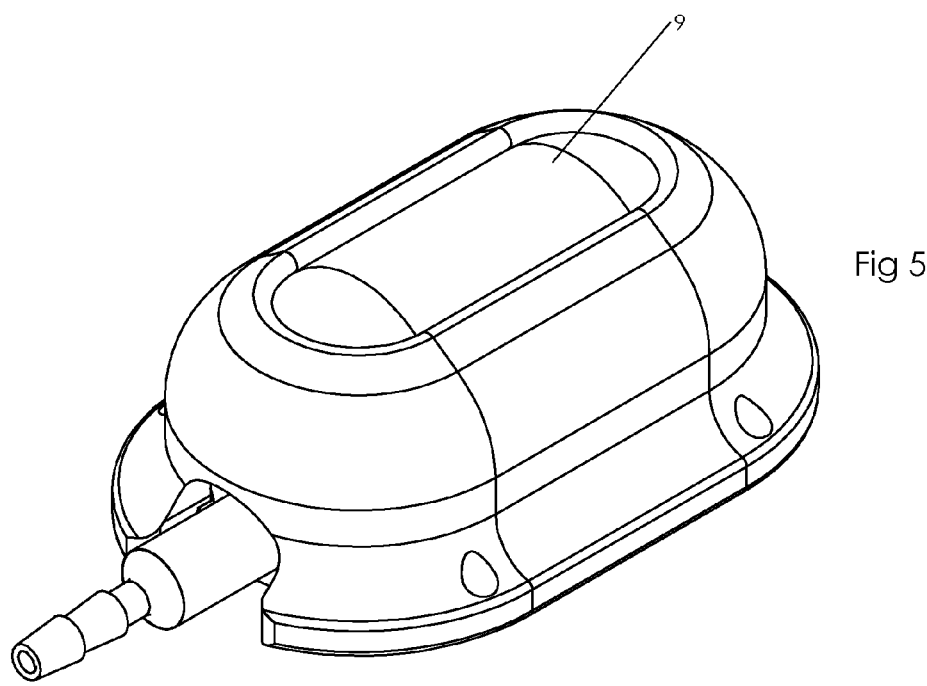
FIG. 5 is an isometric view of an embodiment of the skin parallel vascular access port.
Figure 6:
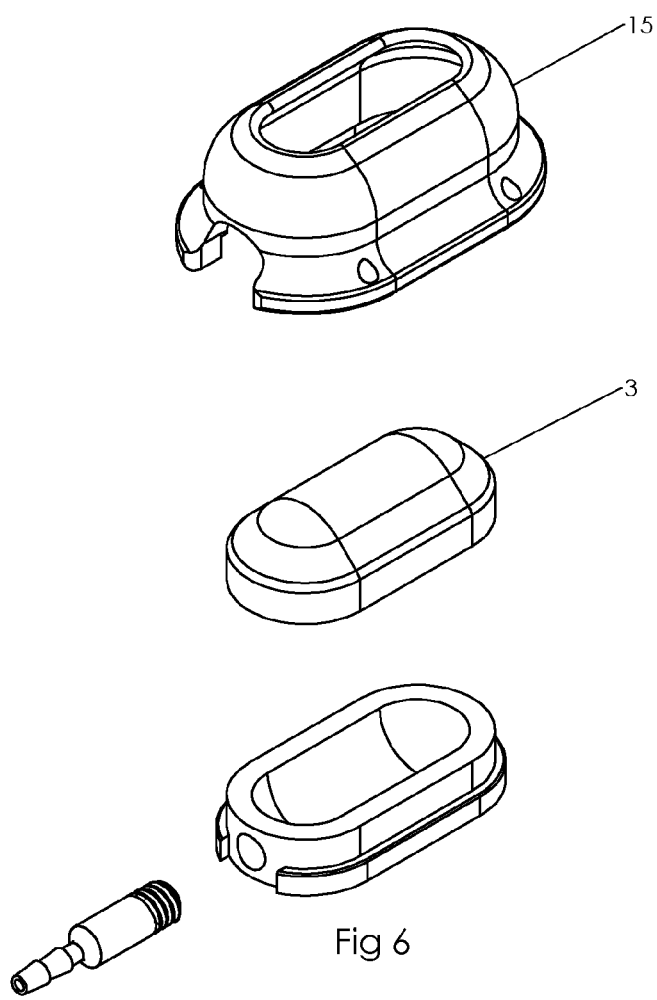
FIG. 6 is an isometric exploded view of an embodiment of the skin parallel vascular access port.

As shown in FIG. 1a, the present invention, shown generally as 1, is comprised of an improved self-sealing septum 3 and an outlet stem 7 leading from the reservoir 5, or chamber, to a catheter (not shown) that is placed into the vascular system.

In one embodiment, as shown as FIG. 1, the self-sealing septum 3 and reservoir 5 are elongated when compared to conventional ports. Such an elongated septum 3 and reservoir 5 provides for an access portion 9 with a greater surface area along the length of the port and therefore a larger area that is exposed to the subcutaneous tissue when compared to a standard port.

In addition to providing a greater access area 9, the novel shape of the septum 3 and reservoir 5 of the present invention preclude any "corners" in the reservoir. In a conventional port, there are "corners" where the side wall of the reservoir meets the bottom wall of the reservoir and also where the top edge of the side wall meets the septum. It is well known and well documented that debris can accumulate at such corners and angular junctions. To solve this problem, the present invention provides a reservoir 5 that is elongated along the axis A-A but is also substantially rounded where the side wall of the reservoir meets the bottom wall of the reservoir and also where the top edge of the side wall meets the septum. The design and shape of the septum 3 and reservoir 5 thereby precludes any angular junctions between the reservoir and the septum. As shown in FIG. 2b in a cross sectional view, the bottom half of the reservoir 11 is hemispherical in shape along the B-B axis and therefore does not present any "corners". According to principles of fluid mechanics, the efficiency of fluid mixing in a container is lower near the walls of the container and especially in any corners where elements of the container wall join together angularly. The more acute the angle, the lower the mixing efficiency. Laminar flow along the walls of the conduit or reservoir enhances the cleansing or clearing of the reservoir. Laminar flow occurs in areas of smooth wall transitions only. The present invention provides a hemispherically shaped reservoir 5 and, consequently, there are no angular junctions between portions of the reservoir 5. The smooth transitions between the top and bottom portions of the reservoir, 11 and 13, enhance the flushing efficiency and fluid dynamics. This principle applies to both flushing and cleansing of the reservoir of a port. After each infusion or blood withdrawal, the reservoir must be flushed of the debris including but not limited to blood, chemotherapeutic agents, or drugs.

Figure 9:
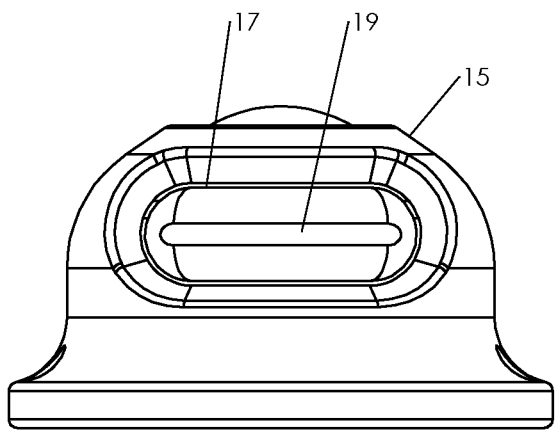
FIG. 9 is a back view of an embodiment of the skin parallel vascular access port.
Figure 10:
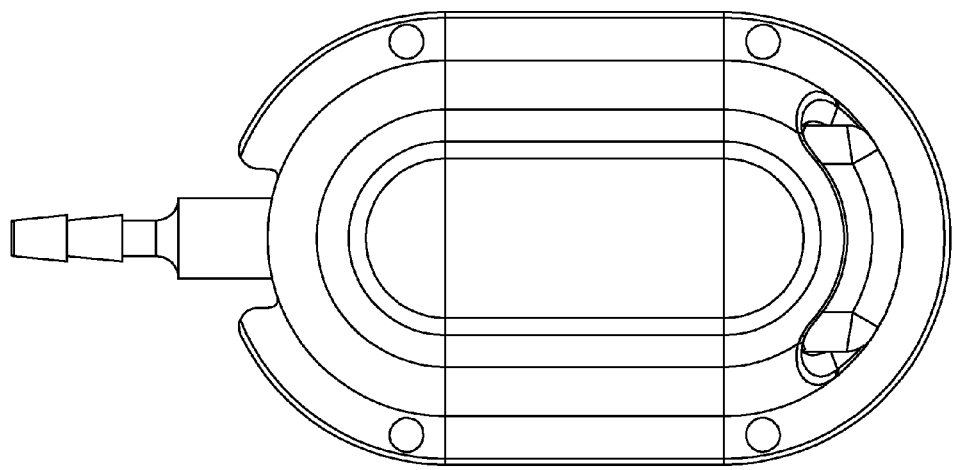
FIG. 10 is a top view of an embodiment of the skin parallel vascular access port.
Figure 11:
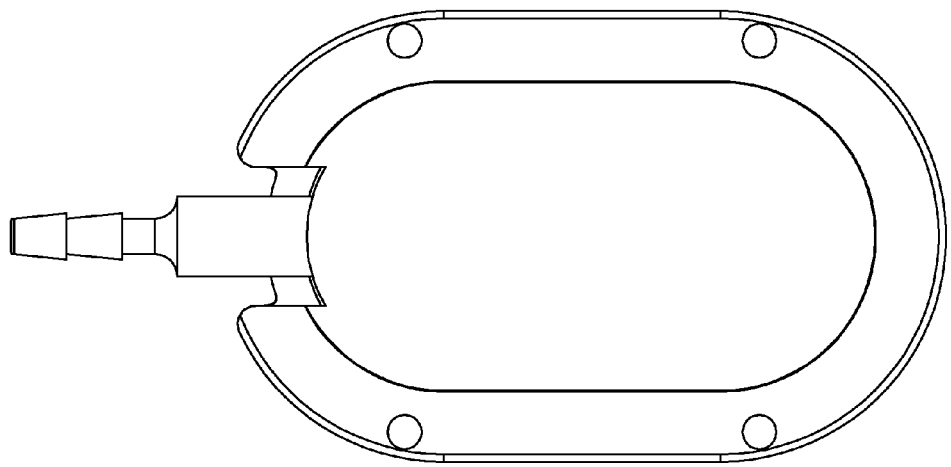
FIG. 11 is a bottom view of an embodiment of the skin parallel vascular access port.
Figure 12:
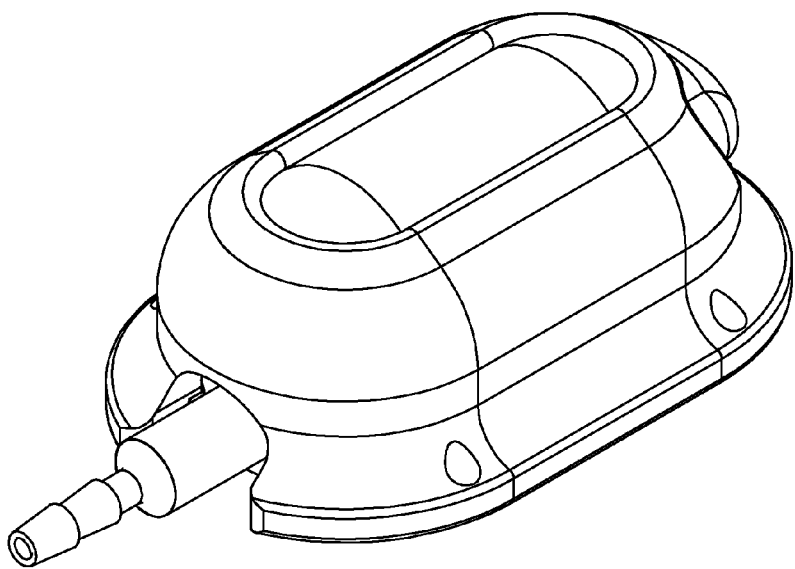
FIG. 12 is an isometric view of an embodiment of the skin parallel vascular access port.
Figure 13:
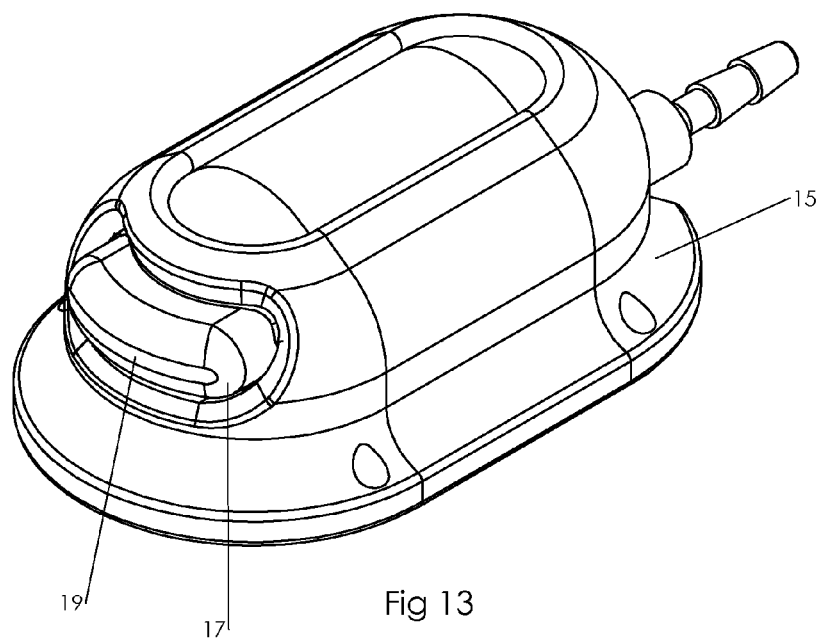
FIG. 13 is a rear isometric view of an embodiment of the skin parallel vascular access port.
Figure 14:
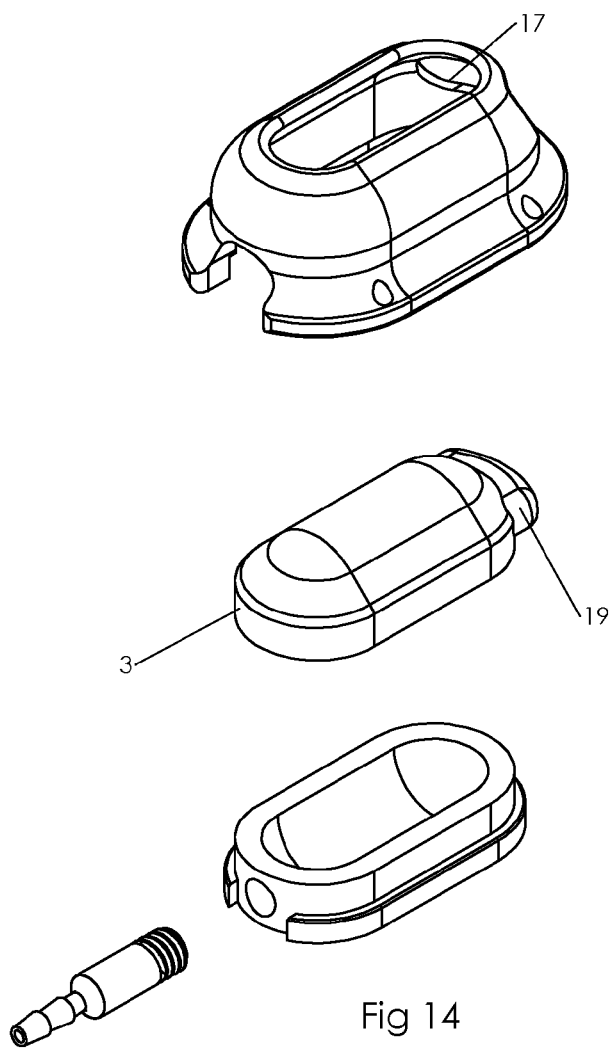
FIG. 14 is an exploded isometric view of an embodiment of the skin parallel vascular access port.
Figure 16A:
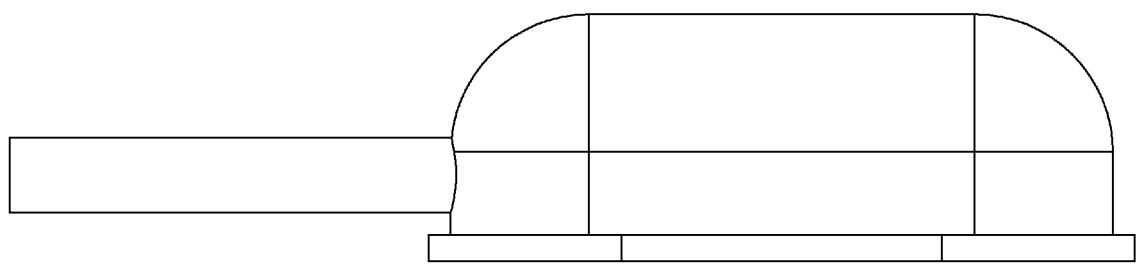
FIG. 16a is a right side view of an embodiment of the skin parallel vascular access port wherein the septum's reservoir or chamber leads to an attached catheter.
Figure 16B:
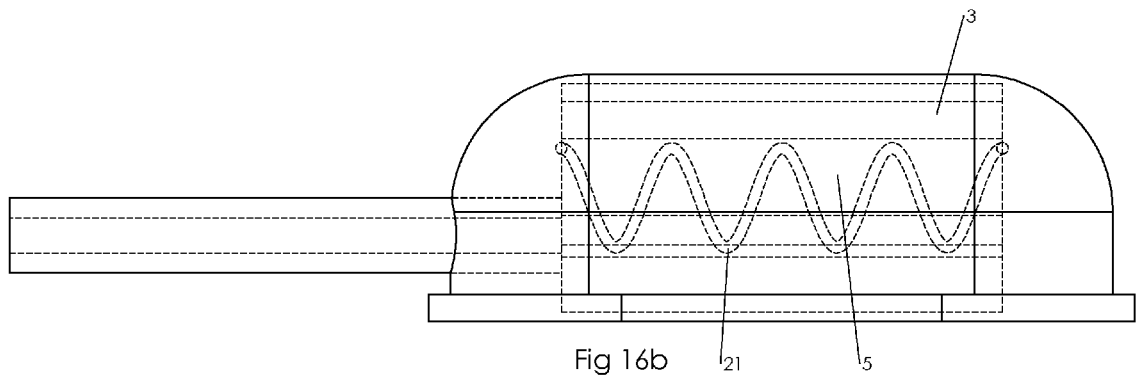
FIG. 16b is a side cross sectional view of an embodiment of the skin parallel vascular access port wherein the septum's reservoir or chamber leads to an attached catheter.
Figure 17:
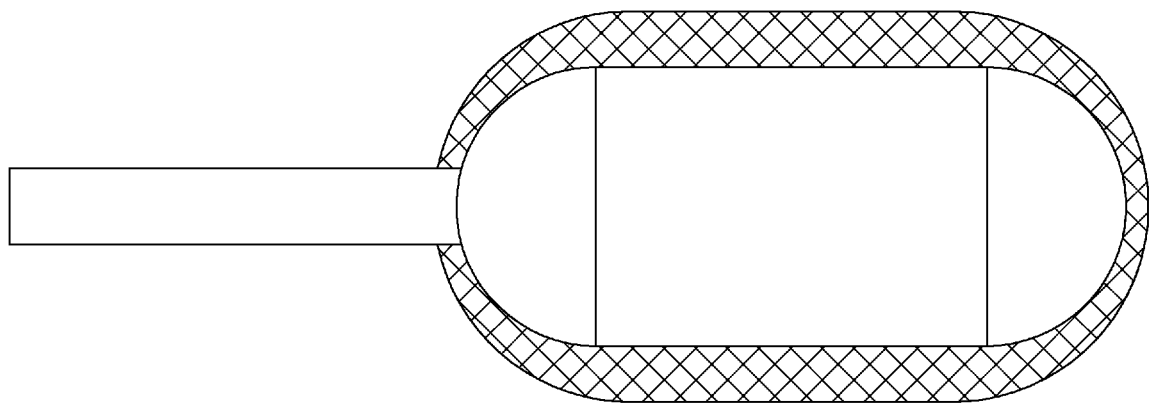
FIG. 17 is a top view of an embodiment of the skin parallel vascular access port wherein the septum's reservoir or chamber leads to an attached catheter.
Figure 18:
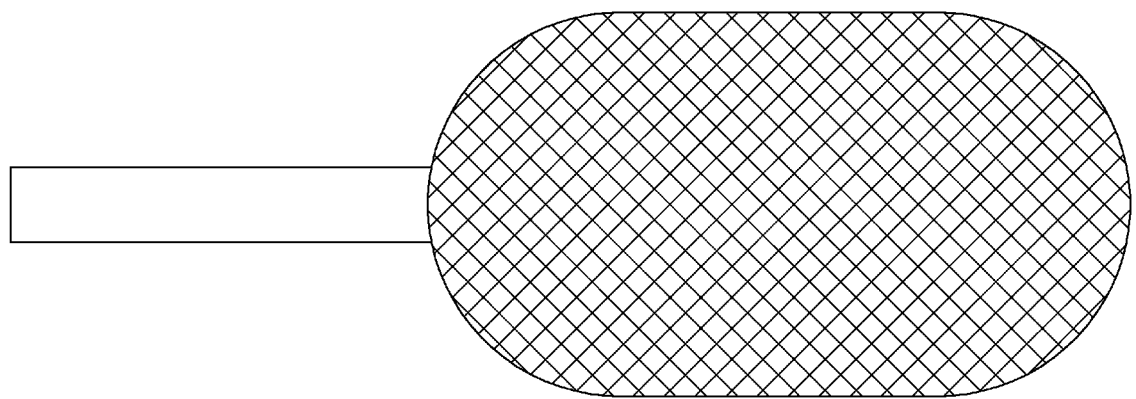
FIG. 18 is a bottom view of an embodiment of the skin parallel vascular access port wherein the septum's reservoir or chamber leads to an attached catheter.
Figure 19:
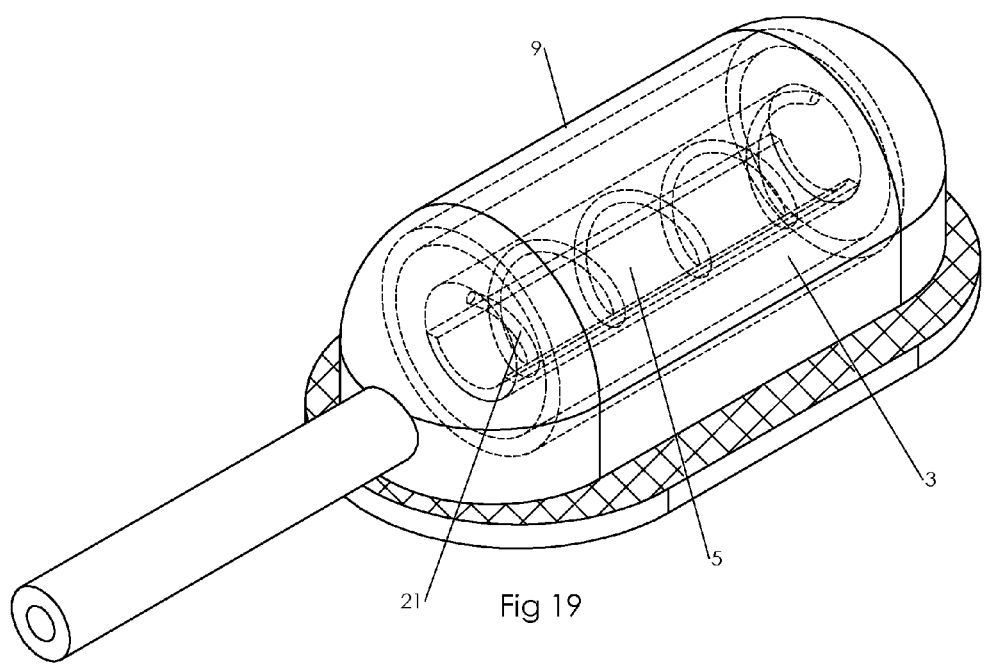
FIG. 19 is an isometric view of an embodiment of the skin parallel vascular access port wherein the lumen and coiled wire appear in broken lines and wherein the septum's reservoir or chamber leads to an attached catheter.

In this embodiment, the septum is constructed by extruding one open-ended tube of silicone and then curing such tube. The tube is then turned inside out such that the original outer surface of the tube is now the inner surface and the surface surrounding the cavity of the tube. The fabricated tube is then cut in half longitudinally to be placed in the septum retainer and pressed onto the rigid reservoir/base. This forms the top half of the reservoir. The sealing capability of the fabricated septum is therefore due to two factors, 1) the compression of the septum due to the internal forces of the reversed septum and 2) the retaining and compressing forces of the septum retainer and reservoir base. The two concepts acting together to create a self-sealing septum are necessary to allow the septum to be elongated and provide a large access area for the caregiver. In one embodiment as shown in FIGS. 7a, 7b, 8a, 8b, 9, 10, 11, 13 and 14, the port body 15 may have an aperture 17 providing an additional access opening to the septum 3. In such embodiment as shown in FIG. 7b, a portion of the septum 19 is fitted into such aperture 17 to allow the user to access the reservoir 5 by introducing an infusion needle through such aperture 17. Unlike conventional ports wherein the a port body provides only one access point to the reservoir, the present invention not only allows a greater access area 9 but allows for an additional access point. As shown in FIG. 9, the aperture 17 may be located on the side of the port body 15 opposite the outlet stem (not shown). Such aperture 17 allows the user to access the reservoir at an angle parallel to the reservoir 5.

In another embodiment, as shown in FIGS. 15b, 19, FIG. 24b, FIG. 25b, and FIG. 28, the self-sealing septum 3 is comprised of a shell-like structure enclosing a fluid reservoir 5 therein. The self-sealing septum 3 may have a large access portion 9 or area that is exposed to the subcutaneous tissue and may be accessed through the use of an infusion needle (not shown). The shell-like structure of the septum 3 allows for a much greater area of the septum 3 exposed to the subcutaneous tissue and thereby creates a much larger area to be accessed by the user. Unlike current vascular access ports wherein the septum 3 is a planar body that is constructed of a single piece molded construction, the septum 3 of the present invention provides for an access portion 9 that is elongated and circular or semi-circular in cross section to not only provide a 180 degree arc in which to axis the septum, but also provides for a greater surface area along the length of the port given the septum's elongated shape. Therefore, the area that is exposed to the subcutaneous tissue when compared to a standard planar septum is quite significant.

In one embodiment, as shown in FIG. 15b, the septum 3 is tubular in shape. The septum is constructed by extruding one open-ended tube of silicone and then curing such tube. The tube is then turned inside out such that the original outer surface of the tube is now the surface surrounding the cavity of the tube. A second silicone closed ended tube is extruded and fitted over the first tube such that the tubes are concentric. The outer diameter of the first tube is slightly larger than the inner diameter of the second tube to provide a compression fit such that the second tube compresses the first tube. The outer surface of the first tube may be bonded to the inner surface of the second tube.

In the present invention, the lumen or cavity of the first tube functions as the reservoir of the vascular access port and may be accessed by using a needle to puncture the wall of both the second tube and first tube, respectively, and then advancing the needle into the lumen or cavity. The user, therefore, introduces the needle through both walls of the second tube and first tube to access the reservoir. Unlike standard ports where the reservoir is formed from a reservoir base that is covered by a septum, the septum of the present invention forms the actual reservoir. In the embodiment illustrated in FIGS. 15b, 19, FIG. 24b, FIG. 25b, and FIG. 28, the reservoir is centric to the walls of the first and second tube. In another embodiment, the reservoir of the present invention is eccentric to the walls of the first and second tubes. By having the reservoir eccentric to the wall of the first and second tubes, the walls of the first and second tubes will be thicker in one area, preferably in the access portion of the septum thereby providing a thicker septum where the septum is accessed.

In the present embodiment, as illustrated in FIGS. 15b, 19, FIG. 24b, FIG. 25b, and FIG. 28 a coiled wire or spring 21 may be inserted into the cavity or lumen of the first tube to prevent the first tube from collapsing and to maintain the uniformity of the cavity. The coiled wire or spring 21 extends the length of the cavity of the first tube to ensure that the cavity maintains a uniform height and circumference along the length of the cavity. Alternatively, a tube or cylinder having a plurality of apertures such as a mesh or grid in the shape of a cylinder may be inserted into the cavity of the first tube to prevent the first tube from collapsing and to maintain the uniformity of the cavity. Alternatively, a rigid or semi-rigid silicone or nonmetal cylinder may be inserted into the cavity of the first tube to prevent the first tube from collapsing and to maintain the uniformity of the cavity wherein said rigid or semi-rigid material is capable of being punctured by a needle.

As shown in FIGS. 24a, 24b, 25a, 25b, 28, 29, 30, and 31, the septum 3 is adhered to a port body 15 in which the bottom portion of the septum is fitted securely. The base has a longitudinal U shaped or hemispherical channel into which the bottom portion of the septum nests. The septum may be adhered to the base using a medical adhesive or may be cured using a medical grade silicone. The purpose of the base is to prevent the advancement of a needle through the port entirely and, therefore, blocks the needle from advancing through to the exterior of the port. The base further possesses a series of suture holes defined within the base to allow the base to be sutured to the underlying muscle and/or tissues of the patient.

The reservoir of the present invention further leads to an outlet stem. In one embodiment, the outlet opening and outlet passageway is positioned on one end of the septum and located along the axis of the septum as shown in FIGS. 1a, 1b, 2a, and 2b.

In one embodiment of the present invention, the reservoir may lead to a second outlet stem, preferably opposite the first outlet stem. The present invention is thus transformed into acting as a conduit to allow fluids to pass from the first outlet stem into the reservoir and then through the second outlet stem.

Figure 20:
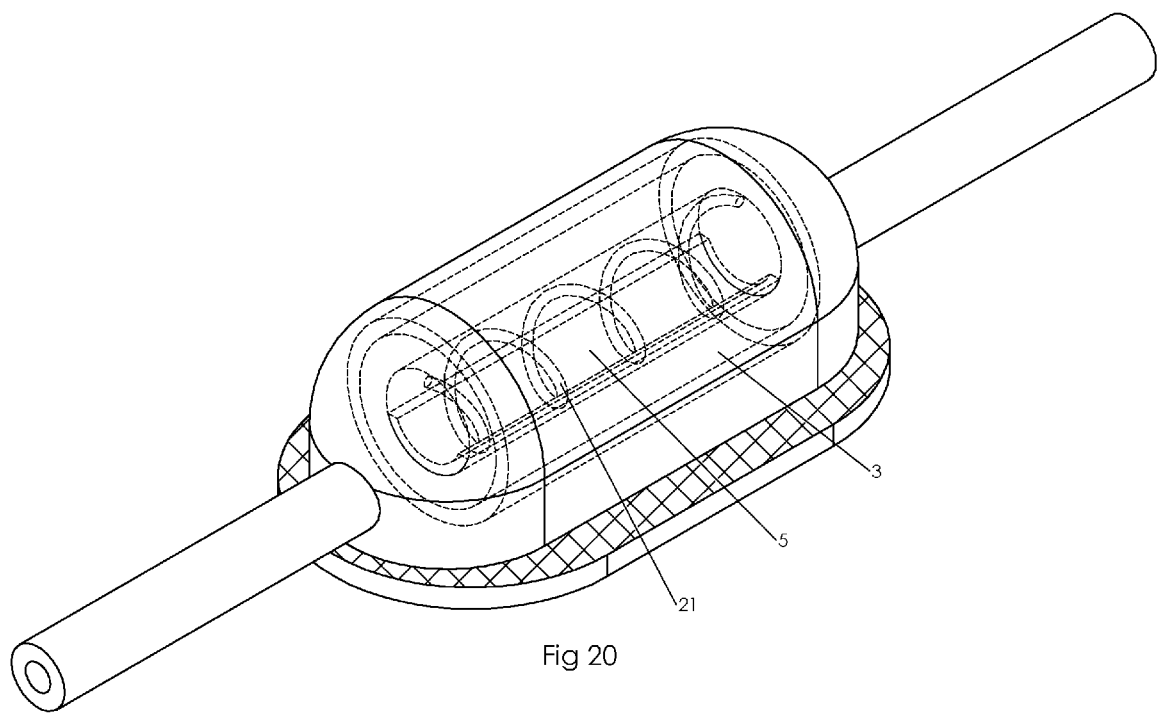
FIG. 20 is an isometric view of an embodiment of the skin parallel vascular access port wherein the lumen and coiled wire appear in broken lines and wherein the septum's reservoir or chamber leads to an attached catheter at each end of the reservoir or chamber.
Figure 22A:
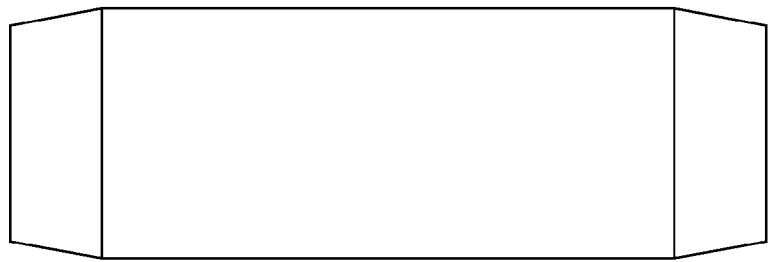
FIG. 22a is a right view of an embodiment of the present invention wherein the present invention is a shunt.
Figure 22B:
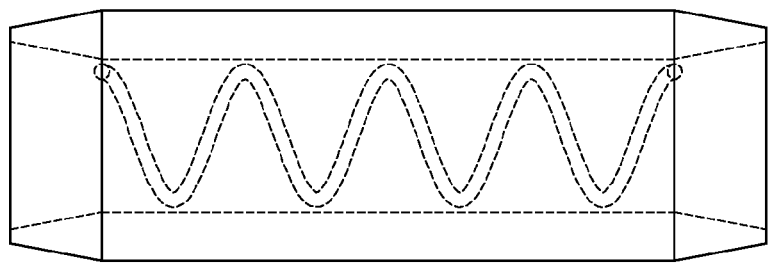
FIG. 22b is a right view of an embodiment of the present invention wherein the present invention is a shunt wherein the lumen and coiled wire appear in broken lines.
Figure 23:
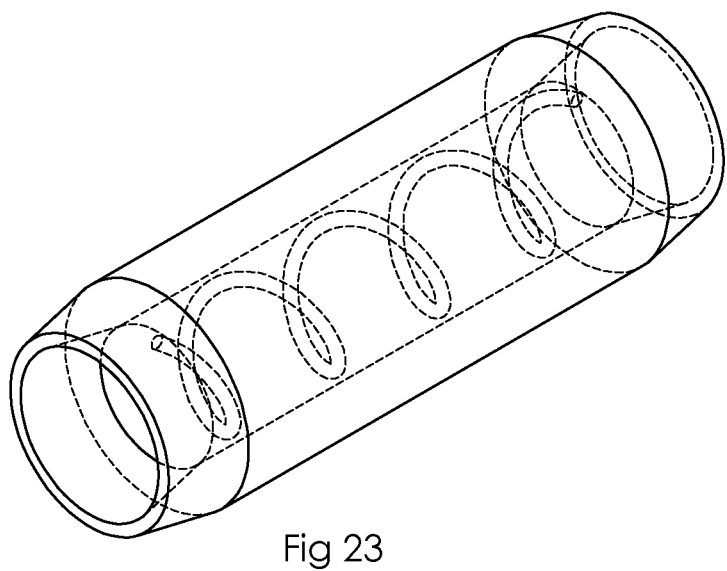
FIG. 23 is an isometric view of an embodiment of the present invention wherein the present invention is a shunt and where the lumen and coiled wire appear in broken lines.
Figure 24A:
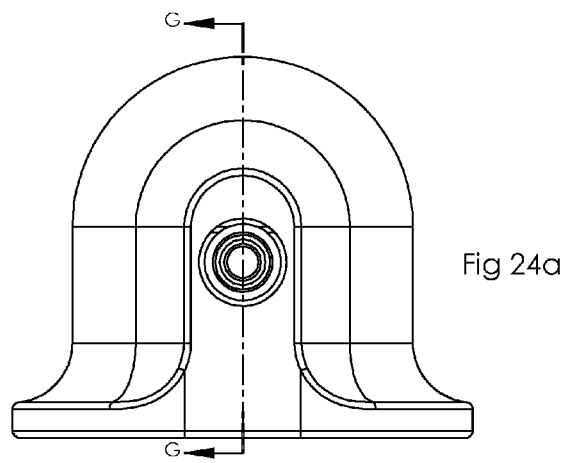
FIG. 24a is a front view of an embodiment of the skin parallel vascular access port.
Figure 24B:
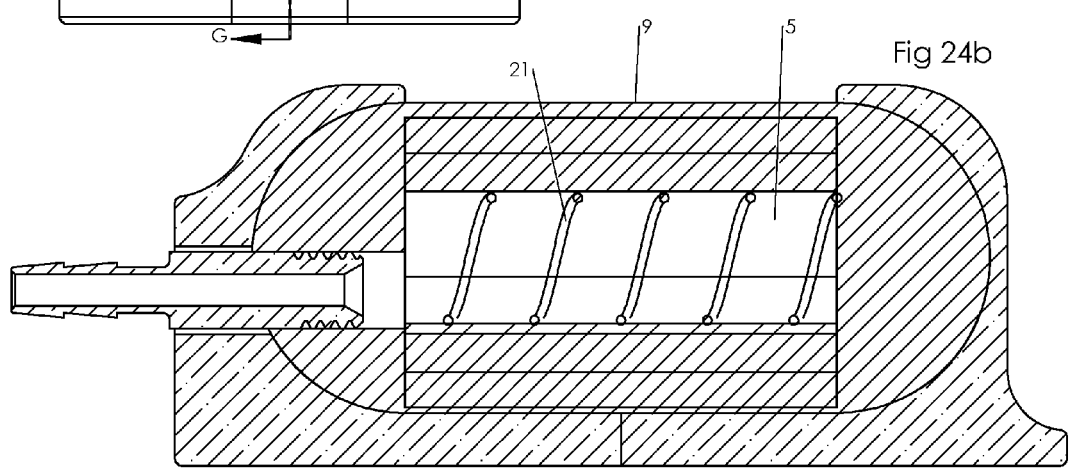
FIG. 24b is a side cross sectional view of an embodiment of the skin parallel vascular access port.
Figure 25A:
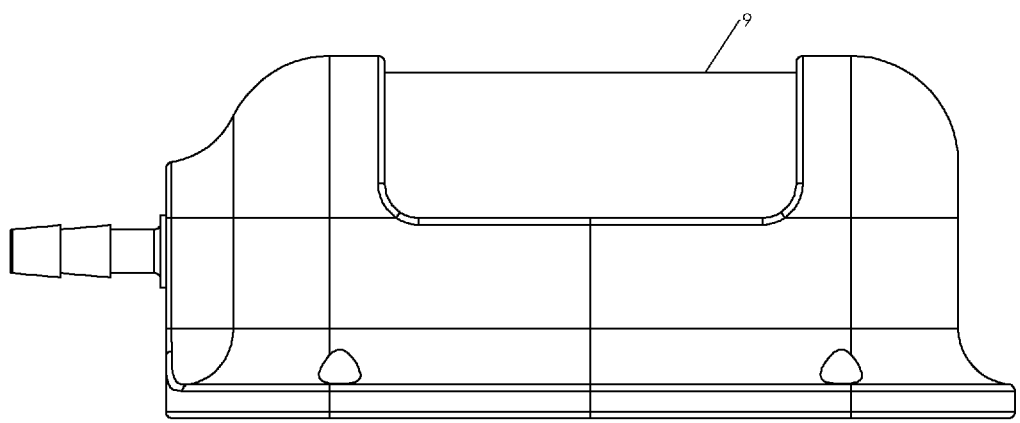
FIG. 25a is right view of an embodiment of the skin parallel vascular access port.
Figure 25B:
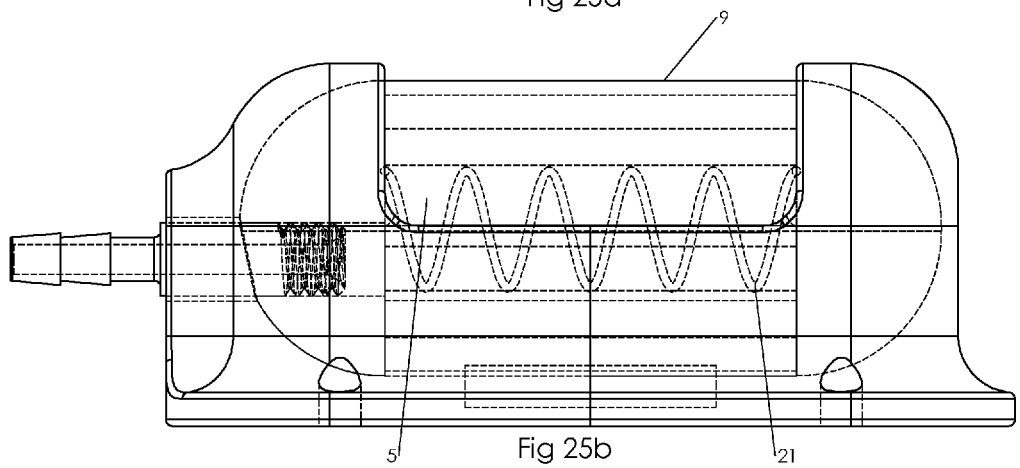
FIG. 25b is a side cross sectional view of an embodiment of the skin parallel vascular access port.
Figure 26:
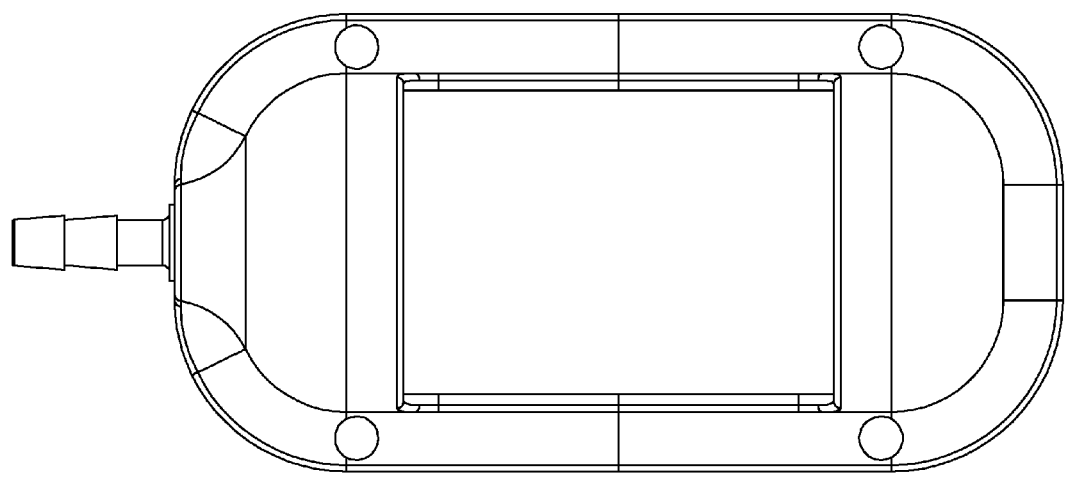
FIG. 26 is a top view of an embodiment of the skin parallel vascular access port.
Figure 27:
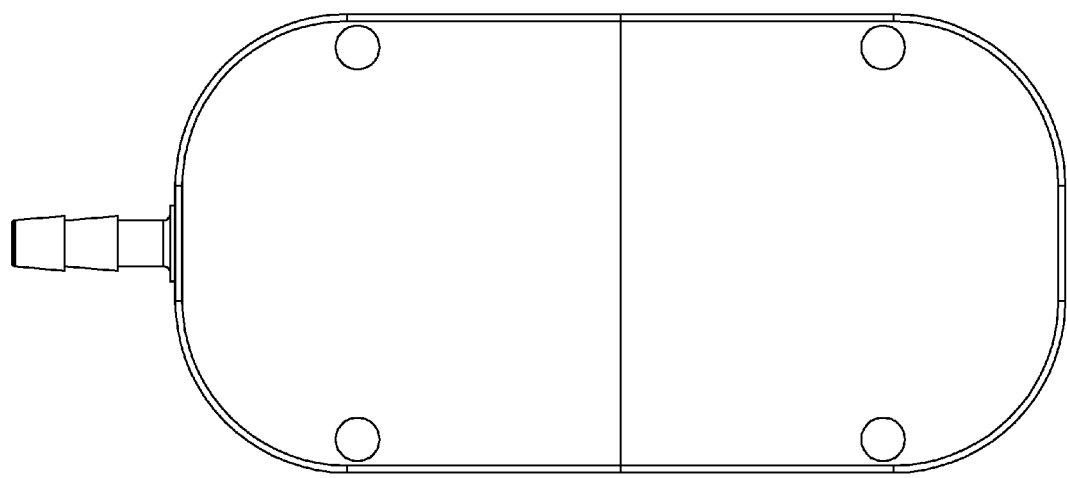
FIG. 27 is a bottom view of an embodiment of the skin parallel vascular access port.
Figure 28:
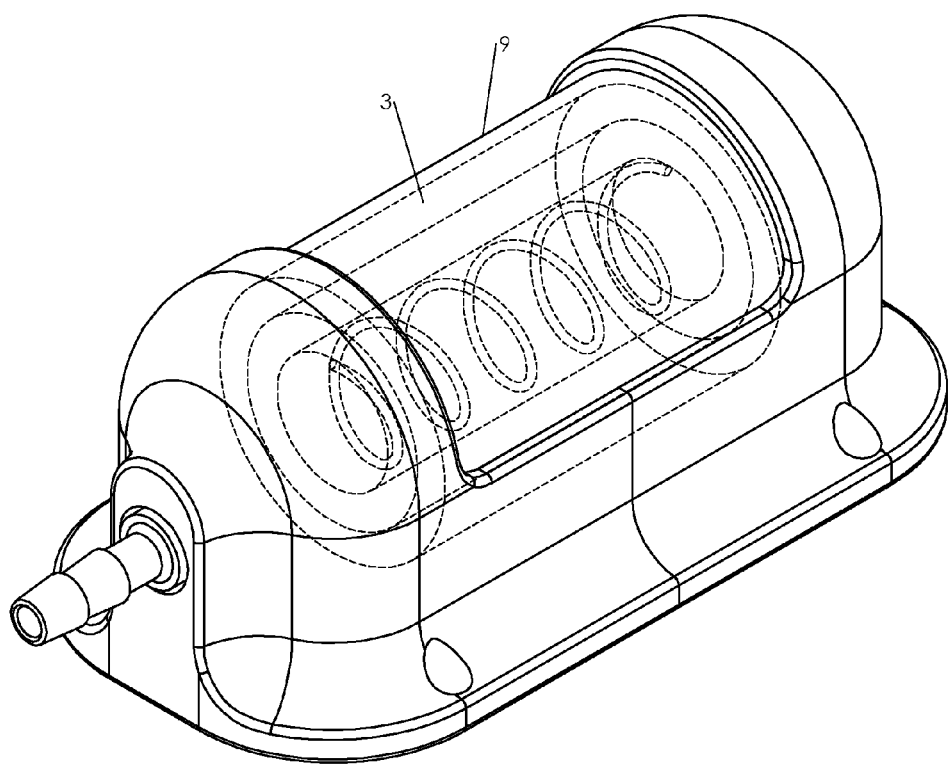
FIG. 28 is an isometric view of an embodiment of the present invention wherein the port is a shunt wherein the lumen and coiled wire appear in broken lines
Figure 29:
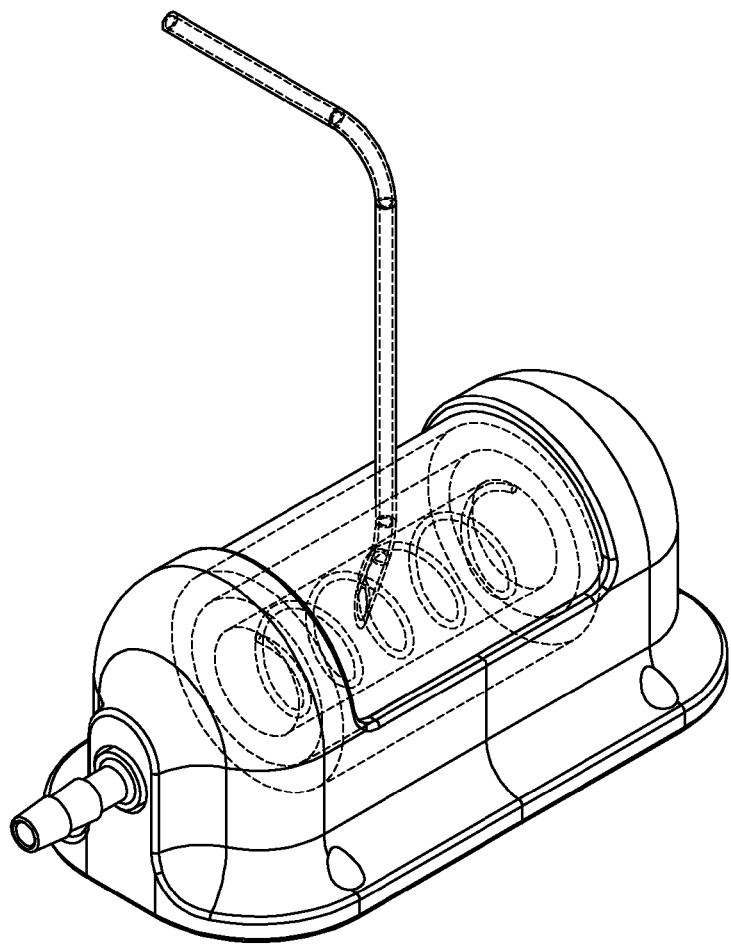
FIG. 29 is an isometric view of a preferred embodiment of the skin parallel vascular access port illustrating a needle introduced into the vascular access port perpendicularly relative to the base.
Figure 30:
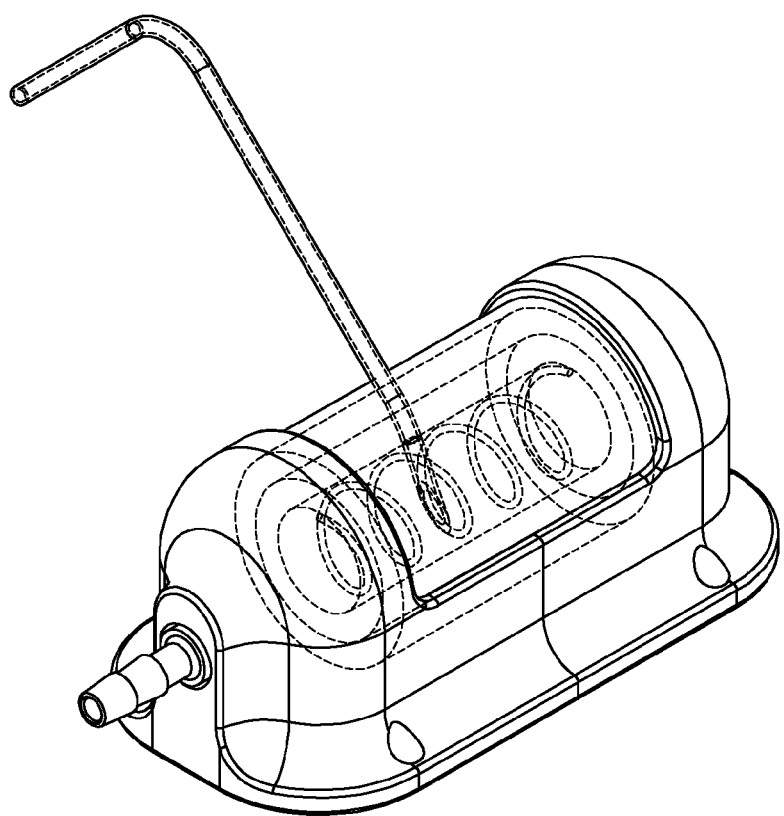
FIG. 30 is an isometric view of a preferred embodiment of the skin parallel vascular access port illustrating a needle introduced into the vascular access port at a 45 degree angle relative to the base and outlet stem.
Figure 31:
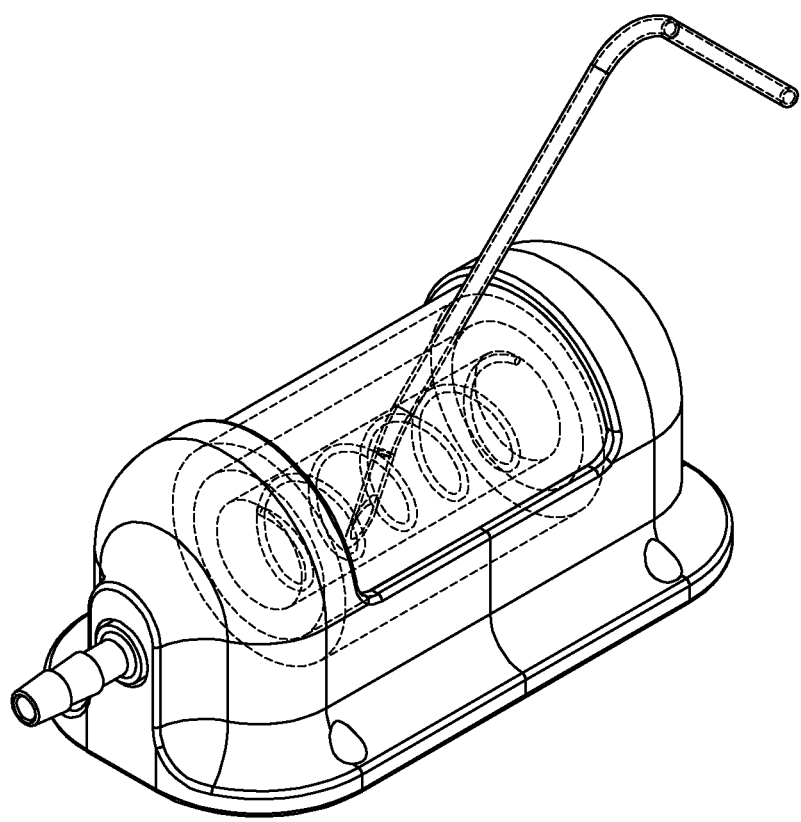
FIG. 31 is an isometric view of a preferred embodiment of the skin parallel vascular access port illustrating a needle introduced into the vascular access port at approximately at a 135 degree angle relative to the base and outlet stem.

In another embodiment, as shown in FIGS. 15b and 20, the base is an impenetrable needle shield 23 that lines the bottom portion of the cavity of the first tube. The purpose of the impenetrable needle shield 23 is to prevent the advancement of a needle through the port entirely and therefore blocks the needle advancing through to the exterior of the port. The impenetrable needle shield 23 may be made of a metal tube that has been cut in half along its axis and imbedded in the cavity off the first tube along the interior bottom surface of the first tube. In such an embodiment, the improved vascular access port possesses a silicone lip 25 around the perimeter of the septum to allow the improved vascular access port to be sutured. Such lip 25 may have a layer comprised of a mesh, such as a Dacron mesh, to provide reinforcement when the port is sutured in place.

The outlet stem 7 is preferably comprised of a biocompatible material, such as electropolished stainless steel, or other surgical grades of steel, to also include a biocompatible hard material such as titanium.

In one embodiment as shown in FIGS. 15b, 16a, 16b, and 19, the reservoir 5 leads directly to a catheter and does not require an outlet stem 7. In another embodiment, the reservoir 5 leads directly to two catheters in opposite directions along the axis of the port body and does not require an outlet stem 7. In another embodiment, as shown in FIGS. 21, 22a, 22b, and 23, the present invention is a shunt wherein the body does not possess an outlet tube or catheter. Although the description above contains much specificity, these should not be construed as limiting the scope of the invention but as merely providing illustrations of some of the presently preferred embodiments of this invention.

We hereby claim:

1. An improved vascular access port comprising:
   a) an elastomeric, needle penetrable cylindrically shaped septum along the longitudinal axis of the port forming a cylindrically shaped reservoir along the longitudinal axis of the port therein within the walls of the septum wherein the reservoir is eccentric to the walls of the septum, further having a support structure within the walls of the septum to maintain the integrity of the reservoir wherein the septum has one tapered closed end and one end leading to an outlet; and
   b) an outlet leading from said reservoir to the exterior of said reservoir wherein the outlet extends axially from the reservoir.

2. An improved vascular access port according to claim 1, wherein the reservoir is concentric to the walls of the septum.

3. An improved vascular access port according to claim 1, wherein the support structure is a coil support extending from the bottom interior wall of the septum to the top interior wall of the septum to maintain the uniformity of the reservoir.

4. An improved vascular access port according to claim 3, wherein an impenetrable needle shield lines the bottom portion of the reservoir.

5. An improved vascular access port according to claim 4, wherein a lip is formed around the bottom periphery of the improved vascular access port.

6. An improved vascular access port according to claim 1, wherein the septum is securely fitted to a base.

7. An improved vascular access port according to claim 1, wherein the base possesses suture holes.

8. An improved vascular access port comprising:
   a) an elastomeric, needle penetrable septum substantially tubular in shape wherein the lumen of the septum forms a reservoir having one closed tapered end and one end leading to an outlet wherein an impenetrable needle shield lines the bottom interior wall of the septum wherein the reservoir is eccentric to the walls of the septum ; and
   b) outlet leading from said reservoir.

9. An improved vascular access port according to claim 8, wherein the reservoir is concentric to the walls of the septum.

10. An improved vascular access port according to claim 8, wherein means for maintaining the uniformity of the reservoir are contained within the reservoir.

11. An improved vascular access port according to claim 10, wherein the septum is securely fitted to a base.

12. An improved vascular access port according to claim 10, wherein the base possesses suture holes.

13. An improved vascular access port according to claim 8, wherein a lip is formed around the bottom periphery of the improved vascular access port.

14. An improved vascular access port comprising:
   a) A rigid base having a bottom portion and a side walls, having one opening at one end for the outlet and one opening at in the top portion of the base extending from the side wall proximal to the outlet to side wall distal to the outlet the end of to provide access to the reservoir wherein the reservoir is characterized by having a longitudinal axis defined by the length between the opening for the outlet and the end of the reservoir opposite of the outlet wherein such length is at least twice the length of the vertical length of the base between the bottom of the of the base and the top of said base;
   b) an elastomeric, needle penetrable cylindrically shaped septum along said longitudinal axis of the port-forming a reservoir therein; and
   c) outlet leading from said reservoir.

15. An improved vascular access port according to claim 14, wherein the septum is cylindrical in shape having one closed end and one end leading to outlet means.

16. An improved vascular access port according to claim 14, wherein the reservoir is concentric to the walls of the septum.

17. An improved vascular access port according to claim 14, wherein the reservoir is eccentric to the walls of the septum.

18. An improved vascular access port according to claim 14, wherein means for maintaining the uniformity of the reservoir are contained within the reservoir.

19. An improved vascular access port according to claim 14, wherein the base possesses suture holes.

20. An improved vascular access port comprising:
   a) a rigid base having a bottom portion and side walls having one opening at one end for an outlet, one opening at the opposite end to allow needle penetrable access, and one opening at the top portion of the base extending from the side wall proximal to the outlet to side wall distal to the outlet the end of to provide access to the reservoir wherein the reservoir is characterized by having a longitudinal axis defined by the length between the opening for the outlet and the end of the reservoir opposite of the outlet wherein such length is at least twice the length of the vertical length of the base between the bottom of the of the base and the top of said base;
   b) an elastomeric, needle penetrable cylindrically shaped septum along the longitudinal axis of the port forming a reservoir therein; and
   c) at least one outlet leading from said reservoir.

21. An improved vascular access port comprising:
a) a reservoir base having a bottom portion and side walls having one opening at one end for an outlet, one opening at the opposite end to allow needle penetrable access, and one opening at the top portion of the base extending from the side wall proximal to the outlet to the side wall distal to the outlet to provide access to the reservoir providing an elongated reservoir along the longitudinal axis of the port;
b) outlet; and
c) an elastomeric, needle penetrable, non-planar, radiused septum wherein the periphery of the septum is located on a lower plane than the top of the septum and wherein the septum is elongated along the longitudinal access of the port forming a concave reservoir and wherein an opening in the septum is an elongated elliptically shaped opening.

22. An improved vascular access port according to claim 21, wherein the septum is radiused.

23. An improved vascular port according to claim 21, wherein the septum is elongated.

24. An improved vascular access port according to claim 21, wherein the cross sectional shape of the reservoir is hemispherical.

25. An improved vascular access port according to claim 21, wherein the port may have at least one additional aperture to access the septum.

26. An improved vascular access port according to claim 21, wherein the exterior of the septum is convex and the interior of the septum is concave.

27. An improved vascular access port according to claim 16, wherein the reservoir base forms a funnel outlet leading to the outlet means.

28. An improved vascular access port according to claim 16, wherein the outlet means are directed along the plane of the bottom wall of the reservoir.

29. An improved vascular access port comprising:
b) a base having a bottom portion and side walls having one opening at one end for the outlet and one opening at the top portion of the base extending from the side wall proximal to the outlet to side wall distal to the outlet the end of to provide access to the reservoir;
b) an elastomeric, needle penetrable cylindrically shaped septum along the longitudinal axis of the port forming a reservoir therein wherein the reservoir is eccentric to the walls of the septum; and
c) outlet leading from said reservoir.

30. An improved vascular access port comprising:
a) an elastomeric, needle penetrable septum substantially tubular in shape wherein the lumen of the septum forms a reservoir having one closed tapered end and one end leading to an outlet wherein an impenetrable needle shield lines the bottom interior wall of the septum and wherein means for maintaining the uniformity of the reservoir are contained within the reservoir; and
b) outlet leading from said reservoir.

31. An improved vascular access port comprising:
a) a rigid reservoir base having a bottom portion and side walls having one opening at one end for an outlet, one opening at the opposite end to allow needle penetrable access, and one opening at the top portion of the base extending from the side wall proximal to the outlet to the side wall distal to the outlet to provide access to the reservoir providing an elongated reservoir along the longitudinal axis of the port wherein the reservoir is characterized by having a longitudinal axis defined by the length between the opening for the outlet and the end of the reservoir opposite of the outlet wherein such length is at least twice the length of the vertical length of the base between the bottom of the of the base and the top of said base;
b) outlet; and
c) an elastomeric, needle penetrable, non-planar, radiused septum wherein the periphery of the septum is located on a lower plane than the top of the septum and wherein the septum is elongated along the longitudinal access of the port forming a concave reservoir.

\* \* \* \* \*